US012697279B2

(12) United States Patent
Patel

(10) Patent No.: US 12,697,279 B2
(45) Date of Patent: Aug. 4, 2026

(54) MEMBRANE FOR CLOSED SYSTEM TRANSFER DEVICE

(71) Applicant: Becton, Dickinson and Company, Franklin Lakes, NJ (US)

(72) Inventor: Romesh Patel, Bridgewater, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 550 days.

(21) Appl. No.: 18/022,903

(22) PCT Filed: Aug. 23, 2021

(86) PCT No.: PCT/US2021/047143
§ 371 (c)(1),
(2) Date: Feb. 23, 2023

(87) PCT Pub. No.: WO2022/046629
PCT Pub. Date: Mar. 3, 2022

(65) Prior Publication Data
US 2023/0301871 A1    Sep. 28, 2023

Related U.S. Application Data

(60) Provisional application No. 63/070,020, filed on Aug. 25, 2020.

(51) Int. Cl.
*A61J 1/14*    (2023.01)
*A61J 1/20*    (2006.01)
*A61M 5/162*    (2006.01)

(52) U.S. Cl.
CPC .............. *A61J 1/1406* (2013.01); *A61J 1/20* (2013.01); *A61M 5/162* (2013.01)

(58) Field of Classification Search
CPC .. A61J 1/20; A61J 1/14; A61M 5/162; A61M 39/00; A61M 39/10; A61M 39/26
See application file for complete search history.

(56) References Cited

U.S. PATENT DOCUMENTS

| | | | |
|---|---|---|---|
| 4,755,173 A | 7/1988 | Konopka et al. | |
| 9,089,475 B2 | 7/2015 | Fangrow | |
| 10,456,329 B2 | 10/2019 | Sanders et al. | |
| 10,744,315 B2 * | 8/2020 | Sanders | A61M 39/1011 |

(Continued)

FOREIGN PATENT DOCUMENTS

| | | |
|---|---|---|
| CN | 102596289 A | 7/2012 |
| EP | 3669930 A1 | 6/2020 |

(Continued)

*Primary Examiner* — Michele Kidwell

(74) *Attorney, Agent, or Firm* — The Webb Law Firm

(57)    ABSTRACT

A membrane for a closed system transfer device includes a first portion including a first material and a second portion including a second material. The first material has different material properties than the second material. The first portion is configured to prevent leakage through the first portion when the first portion is punctured by a cannula for a first predetermined amount of time, and the second portion is configured to prevent leakage through the second portion when the second portion is punctured by the cannula for a second predetermined amount of time. The first predetermined amount of time is larger than the second predetermined amount of time.

12 Claims, 4 Drawing Sheets

(56) References Cited

U.S. PATENT DOCUMENTS

| | | | | |
|---|---|---|---|---|
| 11,779,747 | B2 * | 10/2023 | Sanders | ............. A61M 39/1011 |
| | | | | 604/240 |
| 2008/0053565 | A1 | 3/2008 | Py et al. | |
| 2009/0069783 | A1 * | 3/2009 | Ellstrom | ............... A61J 1/2089 |
| | | | | 604/414 |
| 2012/0179128 | A1 | 7/2012 | Takemoto et al. | |
| 2012/0203193 | A1 | 8/2012 | Rogers | |
| 2015/0123398 | A1 * | 5/2015 | Sanders | ............. F16L 37/0841 |
| | | | | 285/330 |
| 2015/0297454 | A1 | 10/2015 | Sanders et al. | |
| 2015/0297839 | A1 | 10/2015 | Sanders et al. | |

FOREIGN PATENT DOCUMENTS

| | | | | |
|---|---|---|---|---|
| JP | 202062539 A | | 4/2020 | |
| WO | 2008/129550 | * | 10/2008 | ................ A61J 1/14 |

* cited by examiner

MEMBRANE FOR CLOSED SYSTEM TRANSFER DEVICE

CROSS-REFERENCE TO RELATED APPLICATIONS

This application is the United States national phase of International Application No. PCT/US2021/047143 filed Aug. 23, 2021, and claims priority to U.S. Provisional application Ser. No. 63/070,020, entitled "Membrane for Closed System Transfer Device", filed Aug. 25, 2020, the entire disclosures of which are hereby incorporated by reference in their entirety.

BACKGROUND OF THE INVENTION

Field of the Disclosure

The present disclosure relates generally to a membrane for a closed system transfer device.

Description of the Related Art

Health care providers reconstituting, transporting, and administering hazardous drugs, such as cancer treatments, can put health care providers at risk of exposure to these medications and present a hazard in the health care environment. Unintentional chemotherapy exposure can affect the nervous system, impair the reproductive system, and bring an increased risk of developing blood cancers in the future. Some drugs must be dissolved or diluted before they are administered, which involves transferring a solvent from one container to a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists. In order to reduce the risk of health care providers being exposed to toxic drugs, the transfer of these drugs is accomplished utilizing a closed system transfer device or system.

Closed system transfer devices or systems may utilize membranes to ensure the safe transfer of fluid between components. For example, a syringe adapter may include a membrane that contacts a membrane of a mating component, such as a patient connector, IV bag spike, or vial adapter.

SUMMARY OF THE INVENTION

In one aspect or embodiment, a membrane for a closed system transfer device includes a first portion having a first material, and a second portion having a second material, with the first material having different material properties than the second material. The first portion is configured to prevent leakage through the first portion when the first portion is punctured by a cannula for a first predetermined amount of time, and the second portion is configured to prevent leakage through the second portion when the second portion is punctured by the cannula for a second predetermined amount of time. The first predetermined amount of time is larger than the second predetermined amount of time.

The first material may be a thermoplastic elastomer. The second material may be polyisoprene. The first predetermined amount of time may be one hour or greater. The second predetermined amount of time may be 10 seconds or shorter. The first portion and the second portion may be formed separately or integrally. The first portion includes a body having a first side and a second side positioned opposite the first side, with the first portion having a flange extending from the body. The second portion includes a body having a first side and a second side positioned opposite the first side, with the second portion having a flange extending from the body. The flange of the first portion may abut the flange of the second portion.

In a further aspect or embodiment, a patient connector includes a body having a first end and a second end, with the body defining a passageway, a line connection positioned at the second end of the body, and a membrane according to any of the aspects or embodiments discussed above, with the membrane positioned at the first end of the body.

The membrane may be received by an opening defined by the body. The opening may be wider than the passageway, with the body of the first portion extending from the first end of the body, the flange of the first portion positioned within the opening, the body of the second portion positioned within the passageway, and the flange of the second portion positioned within the opening. The body of the patient connector may include a securing extension at the first end of the body, with the securing extension extending radially inward and configured to secure the membrane to the body.

In another aspect or embodiment, a system for the closed transfer of fluid includes a patient connector according to any of the aspects or embodiments discussed above, and a syringe adapter having a housing with a syringe adapter membrane received within the housing and a cannula. The syringe adapter membrane is moveable from a first position within the housing of the syringe adapter to a second positon within the housing when the patient connector is positioned within the housing of the syringe adapter. The membrane of the patient connector is configured to engage the syringe adapter membrane. The cannula is configured to puncture the membrane of the patient connector when the patient connector is positioned within the housing of the syringe adapter.

BRIEF DESCRIPTION OF THE DRAWINGS

The above-mentioned and other features and advantages of this disclosure, and the manner of attaining them, will become more apparent and the disclosure itself will be better understood by reference to the following descriptions of aspects of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
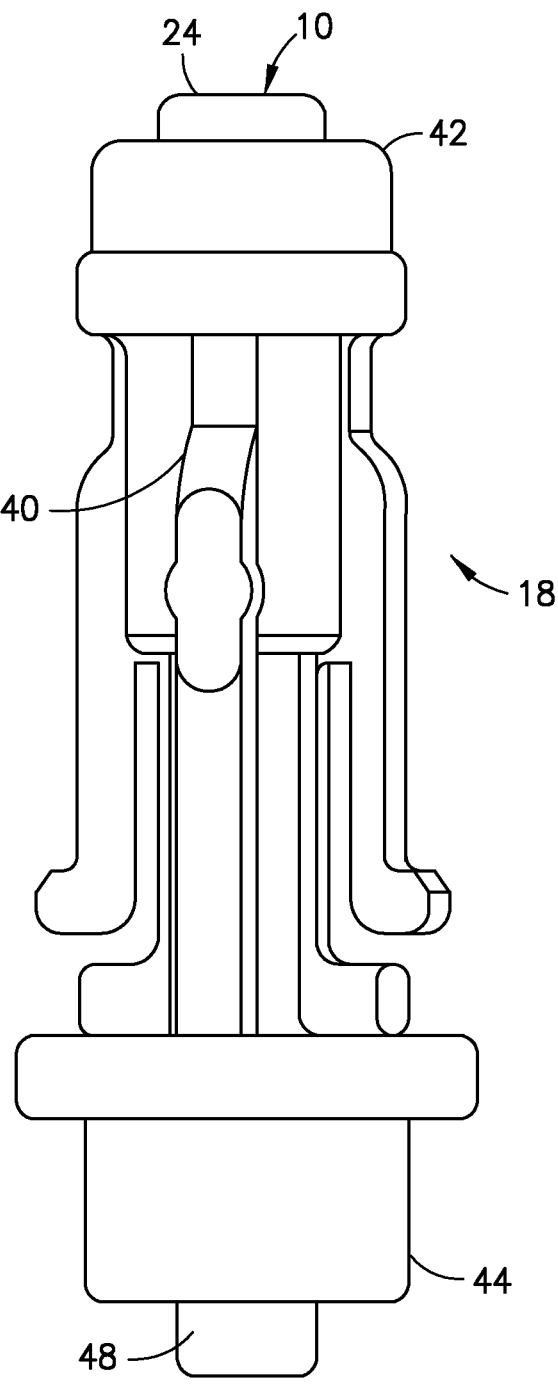
FIG. 1 is a front view of a patient connector according to one aspect or embodiment of the present application.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 2:
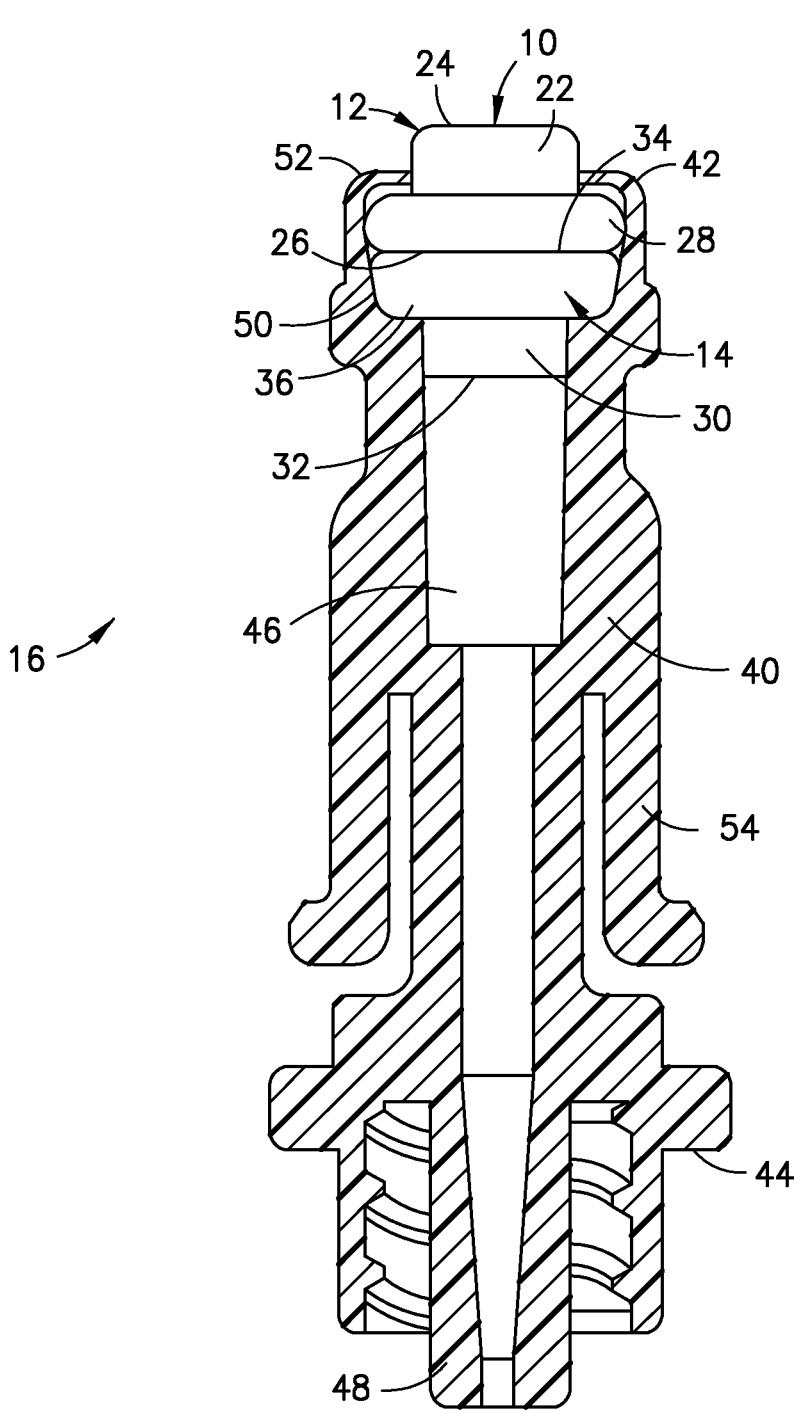
FIG. 2 is a cross-sectional view of the patient connector of FIG. 1.
Figure 3:
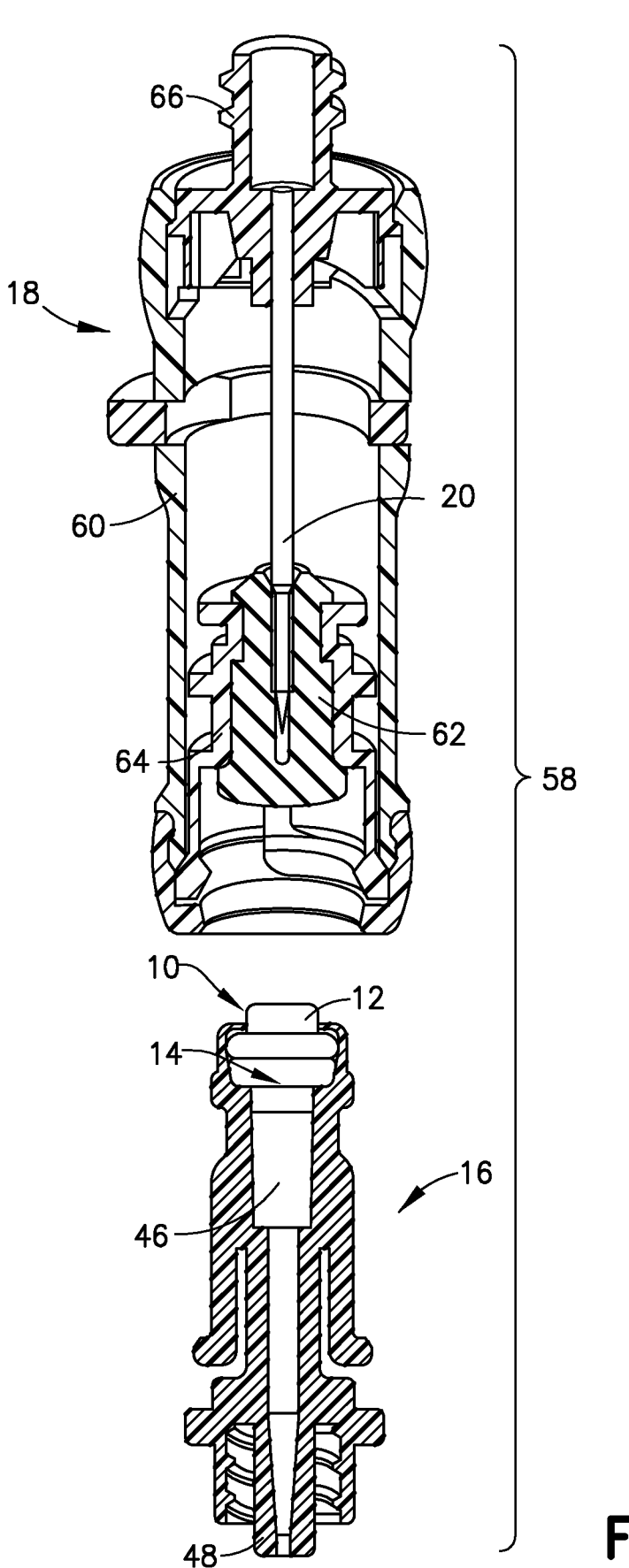
FIG. 3 is a cross-sectional view of the patient connector of FIG. 1, showing the patient connector being inserted into a syringe adapter.

Referring to FIGS. 1-4, a membrane 10 for a closed system transfer device according to one aspect or embodiment of the present application includes a first portion 12 having a first material and second portion 14 having a second material. As shown in FIGS. 1 and 2, the membrane 10 is shown in connection with a patient connector 16, which is utilized to connect one component of a closed system transfer device or system to a patient intravenous line. For example, the patient connector 16 may be connected to a syringe adapter 18 to facilitate the transfer of fluid from one container, such as a syringe barrel, to another container or line, such as an intravenous line, IV bag, or other component. The membrane 10 may be utilized in any component of a closed system transfer device or system. In one aspect or embodiment, the membrane 10 is utilized in each component that mates with the syringe adapter 18, such as the patient connector 16, vial adapter, IV bag spike, etc. The syringe adapter 18 may be the same and operate in the same manner as the syringe adapter shown and described in United States Patent Application Publication No. 2015/0297454, which is hereby incorporated by reference in its entirety.

Referring to FIGS. 1 and 2, the first material of the first portion 12 of the membrane 10 has different material properties than the second material of the second portion 14. The first portion 12 is configured to prevent leakage through the first portion 12 when the first portion 12 is punctured by a cannula 20 for a first predetermined amount of time, and the second portion 14 is configured to prevent leakage through the second portion 14 when the second portion 14 is punctured by the cannula 20 for a second predetermined amount of time. The first predetermined amount of time is larger than the second predetermined amount of time. The first material is a thermoplastic elastomer, although other suitable materials may be utilized. In one aspect or embodiment, the first material may be DRYFLEX® thermoplastic elastomer available from HEXPOL TPE. The second material is a polyisoprene, although other suitable materials may be utilized.

In one aspect or embodiment, the first predetermined amount of time is one hour or greater. In one aspect or embodiment, the second predetermined amount of time is 10 seconds or shorter. In certain configurations, the first predetermined amount of time could be on the order of 24 hours and intended to prevent "long-term" leakage, and the second predetermined about of time could be on the order of a few second to a minute for preventing "short-term" leakage. As noted above, the membrane 10 is utilized in connection with a closed system transfer device or system and, during use, the cannula 20 of the syringe adapter 18 may puncture the membrane 10 and quickly, such as a time period of 10 seconds or shorter, be withdrawn from the membrane. The membrane 10 may also be utilized in scenarios where the cannula 20 of the syringe adapter 18 punctures the membrane 10 and remains in the punctured position for an extended period of time, such as one hour or greater. The membrane 10 is configured to prevent leakage through the membrane 10, such as through an opening caused by the cannula 20 puncturing the membrane 10 or through an interface between the cannula 20 and the membrane 10. The first portion 12 of the membrane 10 is configured to optimize sealing performance for the scenario where the membrane 10 is punctured and remains punctured for the first predetermined amount of time. The second portion 14 of the membrane 10 is configured to optimize sealing performance for the scenario where the membrane 10 is punctured for the second predetermined amount of time. Accordingly, the membrane 10 with the first and second portions 12, 14 is configured to reduce leakage in both long-term and short-term puncturing scenarios.

In one aspect or embodiment, the first portion 12 and the second portion 14 are formed separately. The first portion 12 and the second portion 14 may also be formed integrally. The first portion 12 and the second portion 14 each include a body 22, 30 having a first side 24, 32 and a second side 26, 34 positioned opposite the first side 24, 32 with a flange 28, 36 extending from the body 22, 30. As shown in FIG. 2, the flange 28 of the first portion 12 abuts the flange 36 of the second portion 14. The first and second portions 12, 14 of the membrane 10 may be circular, although other suitable shapes and configurations may be utilized. The first portion 12 may be secured to the second portion 14 via an adhesive or any other suitable arrangement.

Referring again to FIGS. 1 and 2, the patient connector 16 includes a body 40 having a first end 42 and a second end 44, with the body 40 defining a passageway 46, a line connection 48 positioned at the second end 44 of the body 40, and the membrane 10 positioned at the first end 42 of the body 40. The line connection 48 may be a luer lock connection, although other suitable connections may be utilized. The membrane 10 is received by an opening 50 defined by the body 40 of the patient connector 16. The opening 50 of the patient connector 16 is wider than the passageway 46, with the body 22 of the first portion 12 of the membrane 10 extending from the first end 42 of the body 40 and the flange 28 of the first portion 12 positioned within the opening 50. The body 30 of the second portion 14 of the membrane 10 is positioned within the passageway 46 and the flange 36 of the second portion 14 is positioned within the opening 50. The body 40 of the patient connector 16 includes a securing extension 52 at the first end 42 of the body 40, with the securing extension 52 extending radially inward and configured to secure the membrane 10 to the body 40 of the patient connector 16. The patient connector 16 also includes a locking arrangement 54 configured to secure the patient connector 16 to the syringe adapter 18.

Figure 4:
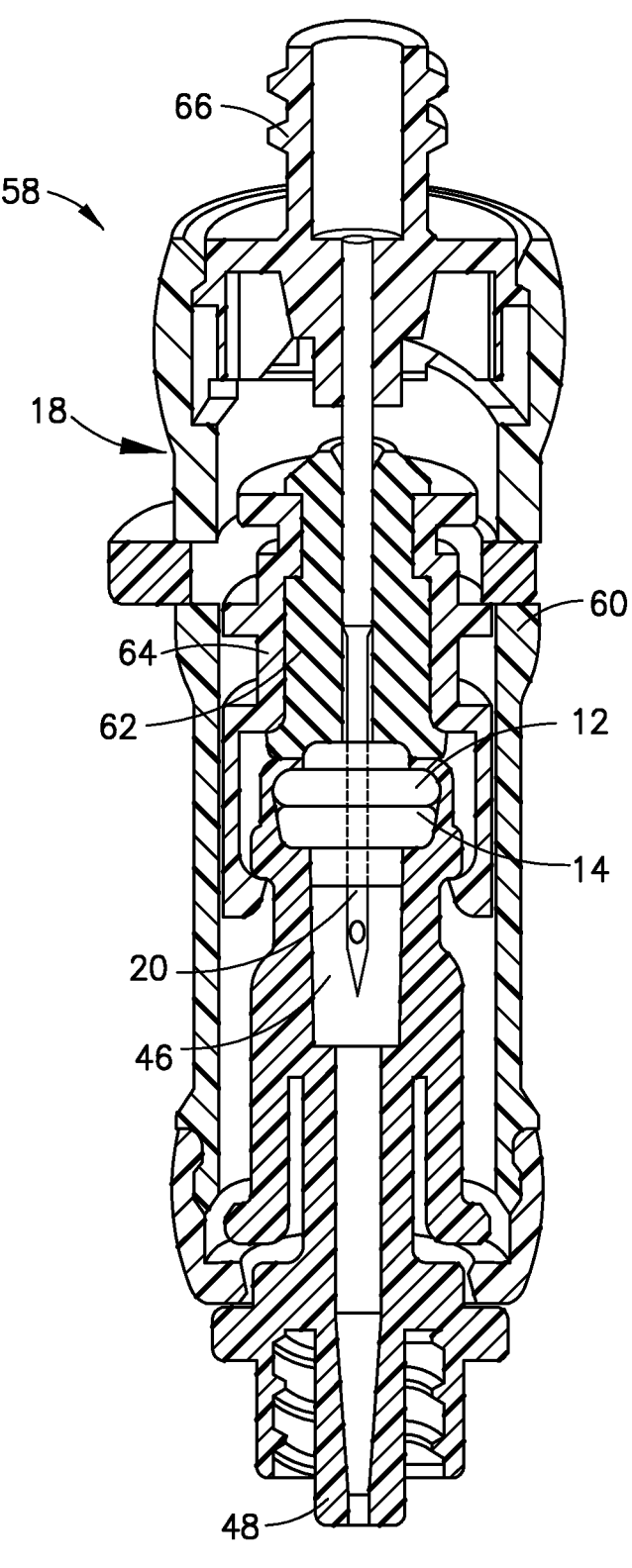
FIG. 4 is a cross-sectional view of the patient connector of FIG. 1, showing the patient connector inserted into a syringe adapter.

In a further aspect or embodiment, a system 58 for the closed transfer of fluid includes the patient connector 16 and the syringe adapter 18, although the system 58 may also include other components of a closed system transfer device or system. The syringe adapter 18 includes a housing 60 having a syringe adapter membrane 62 received within the housing 60 and the cannula 20. The syringe adapter membrane 62 is moveable from a first position within the housing 60 of the syringe adapter 18 to a second positon within the housing 60 when the patient connector 16 is positioned within the housing 60 of the syringe adapter 18, as shown in FIG. 4. The membrane 10 of the patient connector 16 is configured to engage the syringe adapter membrane 62. The cannula 20 is configured to puncture the membrane 10 of the patient connector 16 when the patient connector 16 is positioned within the housing 60 of the syringe adapter 18. The syringe adapter membrane 62 is received by a collet 64, although other suitable arrangements may be utilized. The syringe adapter 18 includes a luer connector 66 configured to be secured to a syringe barrel. The operation of the syringe adapter 18 is described in United States Patent Application Publication No. 2015/0297454.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims. To the extent possible, one or more features of any aspect or embodiment discussed above can be combined with one or more features of any other aspect or embodiment.

What is claimed is:

1. A membrane for a closed system transfer device comprising: a first portion comprising a first body and a first flange extending from the first body, a first material wherein the first material comprises a thermoplastic elastomer; and a second portion comprising a second body and a second flange extending from the second body, a second material wherein the second material comprises a polyisoprene, the first material having different material properties than the second material, wherein the first portion is configured to prevent leakage through the first portion when the first portion is punctured by a cannula for a first predetermined amount of time, and wherein the second portion is configured to prevent leakage through the second portion when the second portion is punctured by the cannula for a second predetermined amount of time, the first predetermined amount of time is larger than the second predetermined amount of time, wherein the first body has a width and the first flange has a width, the width of the first flange is wider than the width of the first body, the second body has a width and the second flange has a width, the width of the second flange is wider than the width of the second body, and the first flange abuts the second flange such that the first flange and the second flange separate the first body and the second body.

2. The membrane of claim 1, wherein the first predetermined amount of time is one hour or greater.

3. The membrane of claim 1, wherein the second predetermined amount of time is 10 seconds or shorter.

4. The membrane of claim 1, wherein the first portion and the second portion are formed separately.

5. The membrane of claim 1, wherein the first portion and the second portion are formed integrally.

6. The membrane of claim 1, wherein the first body has a first side and a second side positioned opposite the first side.

7. The membrane of claim 1, wherein the second body has a first side and a second side positioned opposite the first side.

8. A patient connector comprising:

a body having a first end and a second end, the body defining a passageway;

a line connection positioned at the second end of the body; and a membrane according to claim 1 positioned at the first end of the body.

9. The patient connector of claim 8, wherein the membrane is received by an opening defined by the body.

10. The patient connector of claim 9, wherein the opening is wider than the passageway, the body of the first portion extending from the first end of the body, the flange of the first portion positioned within the opening, the body of the second portion positioned within the passageway, and the flange of the second portion positioned within the opening.

11. The patient connector of claim 10, wherein the body of the patient connector comprises a securing extension at the first end of the body, the securing extension extending radially inward and configured to secure the membrane to the body.

12. A system for the closed transfer of fluid comprising:

a patient connector according to claim 8; and a syringe adapter comprising a housing having a syringe adapter membrane received within the housing and a cannula, the syringe adapter membrane moveable from a first position within the housing of the syringe adapter to a second position within the housing when the patient connector is positioned within the housing of the syringe adapter, wherein the membrane of the patient connector is configured to engage the syringe adapter membrane, and wherein the cannula is configured to puncture the membrane of the patient connector when the patient connector is positioned within the housing of the syringe adapter.

* * * * *